Figure 1:
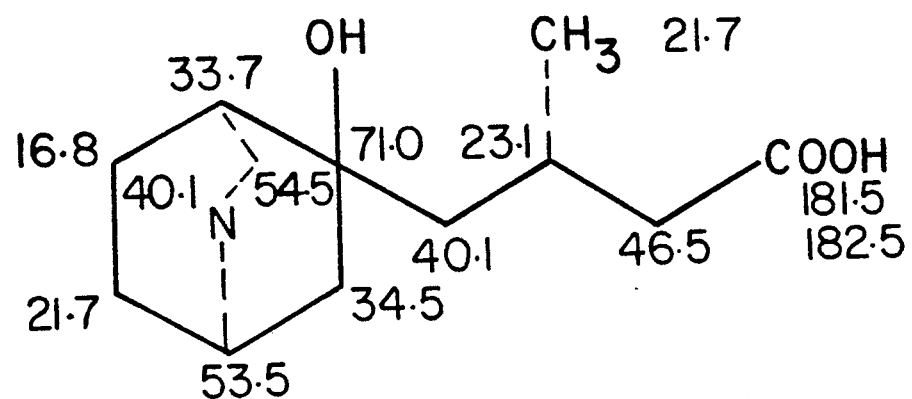

United States Patent [19]

Iwu

[11] Patent Number: 5,019,580

[45] Date of Patent: May 28, 1991

[54] DIOSCORETINE AND ITS USE AS A HYPOGLYCEMIC AGENT

[75] Inventor: Maurice M. Iwu, Unn. Nsukka, Nigeria

[73] Assignee: Shaman Pharmaceuticals, Inc., San Carlos, Calif.

[21] Appl. No.: 452,902

[22] Filed: Dec. 19, 1989

[51] Int. Cl.$^5$ .................. C07D 221/00; A61K 31/435
[52] U.S. Cl. ...................................... 514/299; 546/183; 514/866
[58] Field of Search ......................... 546/183; 514/299

[56] References Cited

PUBLICATIONS

Corley et al. Tet. Lett. 26:1615–1618 (1985).
Undie et al., J. Ethnopharm. 15:133–144 (1986).
Windholz et al. The Merck Index, 10th Edition, 1983, Entry #3298.
Chemical Abstracts, Ring Systems Handbook, 1984.

*Primary Examiner*—Frederick E. Waddell
*Assistant Examiner*—Zinna Northington-Davis
*Attorney, Agent, or Firm*—Pennie & Edmonds

[57] ABSTRACT

A new compound, dioscoretine, as well as the process for making the same is described. According to a preferred embodiment, dioscoretine is derived from the tuber of *Dioscorea dumetorum*. Dioscoretine is a hypoglycemic agent and thus is useful for therapeutic treatment of conditions such as diabetes mellitus.

13 Claims, 4 Drawing Sheets

DIOSCORETINE AND ITS USE AS A HYPOGLYCEMIC AGENT

TABLE OF CONTENTS

1. Field of the Invention
2. Background of the Invention
3. Summary of the Invention
4. Description of the Figures
5. Detailed Description of the Invention
   5.1. Process for Preparing Dioscoretine
   5.2. Characterization of Dioscoretine
   5.3. Uses of Dioscoretine
6. Extraction and Isolation of Dioscoretine
7. Biological Activity of Dioscoretine
   7.1. Hypoglycemic Activity in Normal and Diabetic Animals
   7.2. Acute Toxicity

1. FIELD OF THE INVENTION

This invention relates to a novel biologically active compound, more particularly dioscoretine, isolated originally from tubers of *Dioscorea dumetorum*. The novel compound of the invention is useful as a hypoglycemic agent and thus provides a new and useful agent and pharmaceutical composition for the treatment of diabetes mellitus.

2. BACKGROUND OF THE INVENTION

The common yellow yam *Dioscorea dumetorum* has been used by herbalists and practitioners of West African folk medicine for treatment of diabetes, as a topical anesthetic as well as an arrow poison and as a bait for monkeys (see generally, Corley et al. 1985, Tetrahedron Lett. 26(13):1615-1618). Additionally, *D. dumetorum* tubers are used as famine food, although it is well-known that the yams must be carefully prepared by soaking for several days in running or salt water and boiling overnight. In fact several cases of serious poisoning have resulted from ingestion of improperly prepared tubers (Undie et al., 1986, J. Ethnopharm. 15:133-144).

For use in herbal medicine for treatment of diabetes, a decoction is prepared by steeping the peeled tuber in native gin, distilled from fermented palm wine containing about 30-70% ethanol (termed "kai-kai") for about three days. The decoction is boiled until the color changes from yellow to brown and then is administered to patients in small cupfuls. (Undie et al., supra).

In a preliminary investigation, Undie et al., (supra), have shown that crude extracts of *D. dumetorum* possess hypoglycemic activity when administered to experimental animals. The authors stated, however, that several constituents were present in the extracts and nothing could be known with respect to what constituent was responsible for the observed hypoglycemic effects.

Corley et al. (supra) has shown that a methanol extract of *D. dumetorum* contains alkaloids including dihydrodoiscorine and dumetorine which may have convulsive, toxic activity.

SUMMARY OF THE INVENTION

The present invention provides a novel biologically active compound, dioscoretine, as well as pharmaceutically acceptable salts thereof, which are advantageously used as a hypoglycemic agent. More particularly, the invention provides dioscoretine having the structural formula:

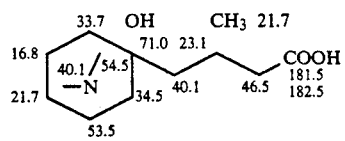

and pharmaceutically acceptable salts thereof.

The invention further encompasses pharmaceutical compositions and methods for using the compound and pharmaceutical compositions for the treatment of Insulin-dependent diabetes mellitus and Non-insulin dependent diabetes mellitus in mammals, including humans.

According to a preferred embodiment of the invention a therapeutically effective hypoglycemic agent is prepared by a method comprising:

(a) extracting a tuber of *Dioscorea dumetorum* with methanol;

(b) concentrating the extract to form a sticky residue;

(c) acidifying the residue with hydrochloric acid;

(d) neutralizing the acidic solution of step (c) and raising the pH to about pH=9;

(e) extracting the basic solution of step (d) with an organic solvent;

(f) collecting the aqueous phase from the extraction of step (e); and (g) eluting the aqueous fraction of step (f) using column chromatography to obtain the biologically active dioscoretine.

4. DESCRIPTION OF THE FIGURES

The present invention may be more fully understood by reference to the following detailed description of the invention, examples of specific embodiments of the invention and the appended figures in which:

FIG. 1 is a representation of the structure of dioscoretine, including $^{13}C$ NMR assignments.

Figure 2:
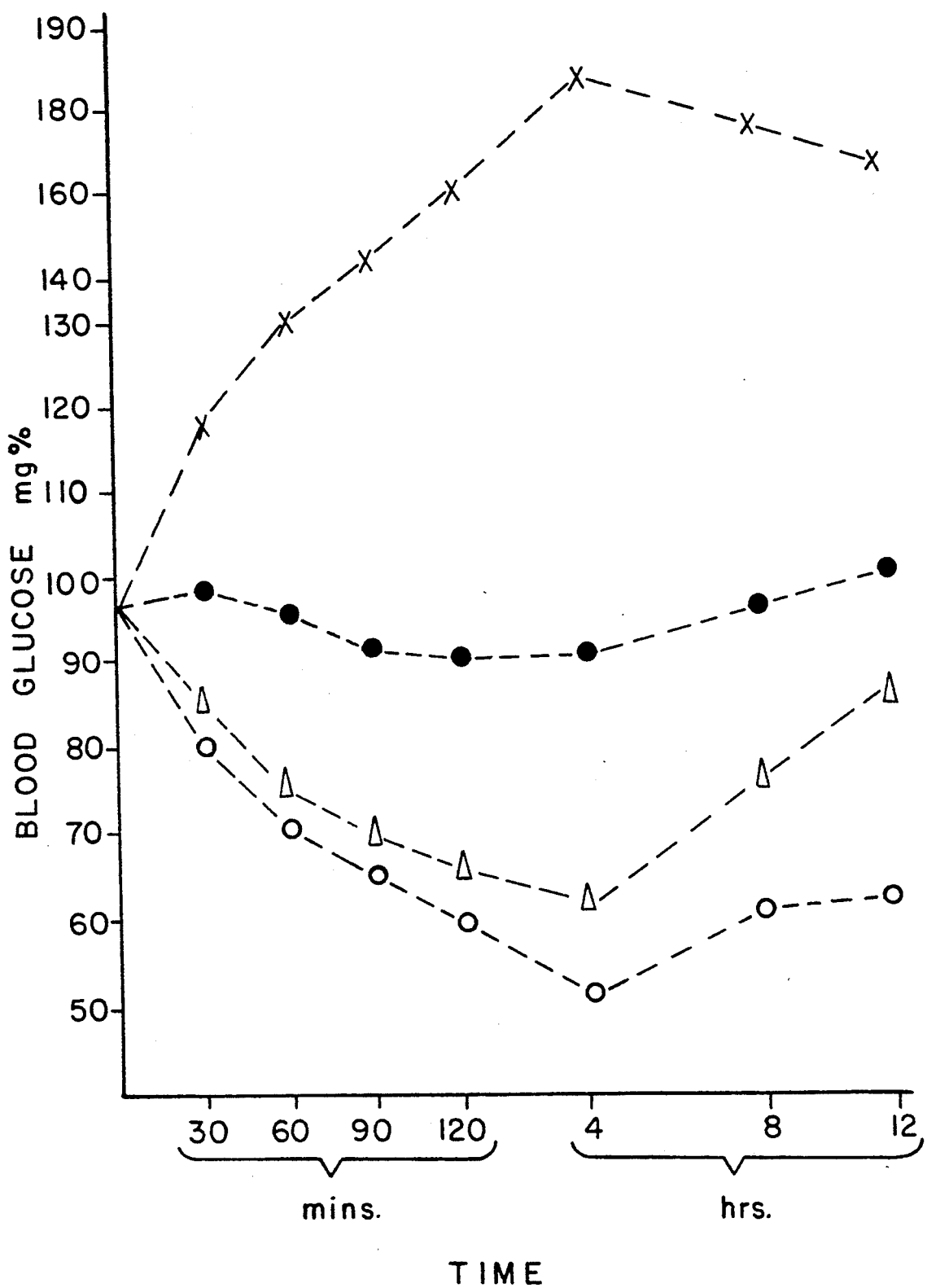

FIG. 2 graphically illustrates the activity of dioscoretine and extracts of *D. dumetorum* on the blood glucose level of normal rats. (o---o) dioscoretine; (△---△) aqueous fraction of the methanol extract; (X---X) chloroform fraction of the methanol extract; (●----●)saline control.

Figure 3:
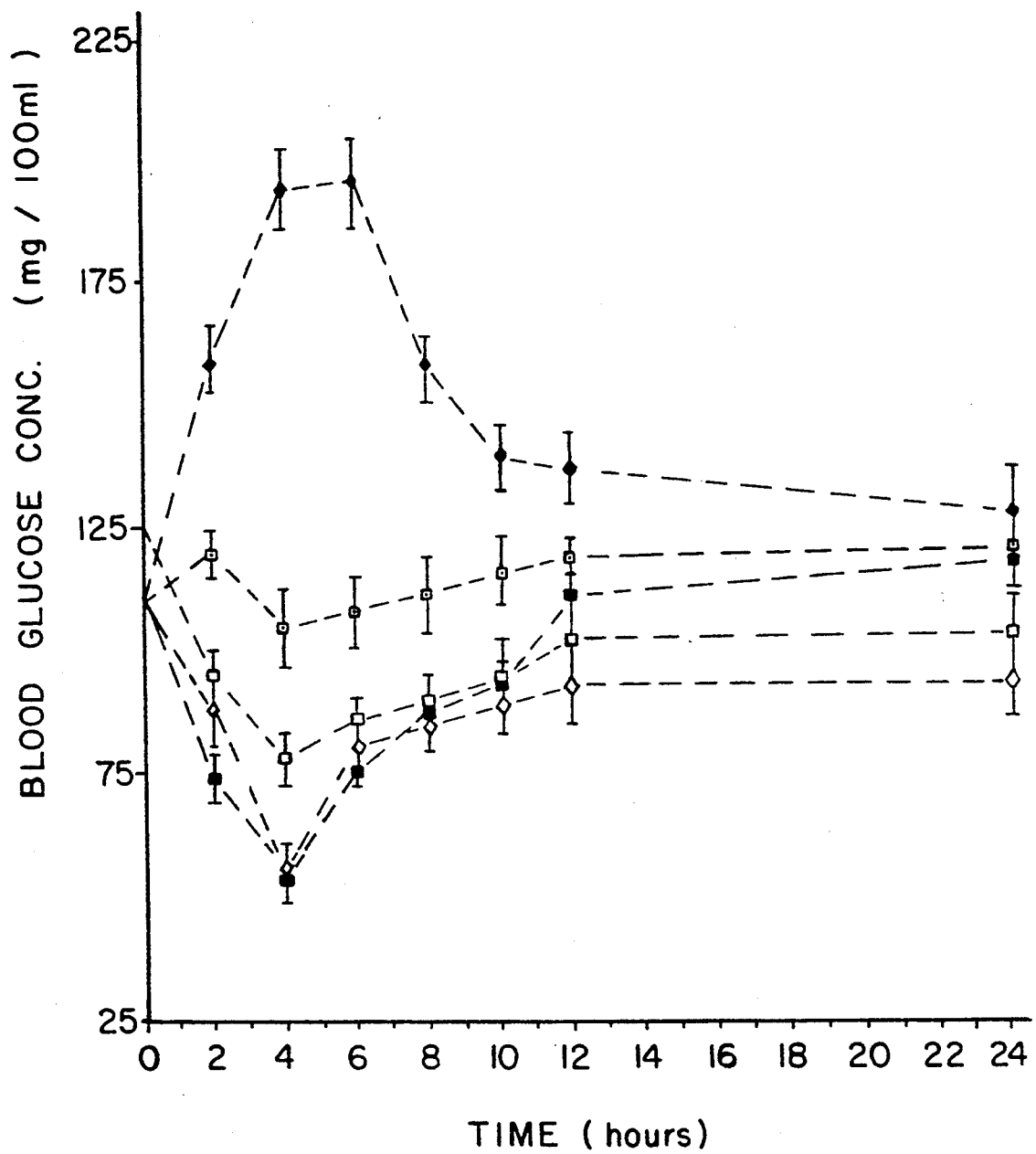

FIG. 3 graphically illustrates the activity of dioscoretine (20 mg/kg) and extracts of D. dumetorum (100 mg/kg) and tolbutamide (500 mg/kg) on the blood glucose level of normal rabbits 12 hour fast. (---▣---) saline control; (---◇---) dioscoretine; (---□---) aqueous fraction of the methanol extract; (---◆---) chloroform fraction of the methanol extract); (---■---) tolbutamide. Values are mean blood glucose expressed as mg/100 ml ±SEM; n=6.

Figure 4:
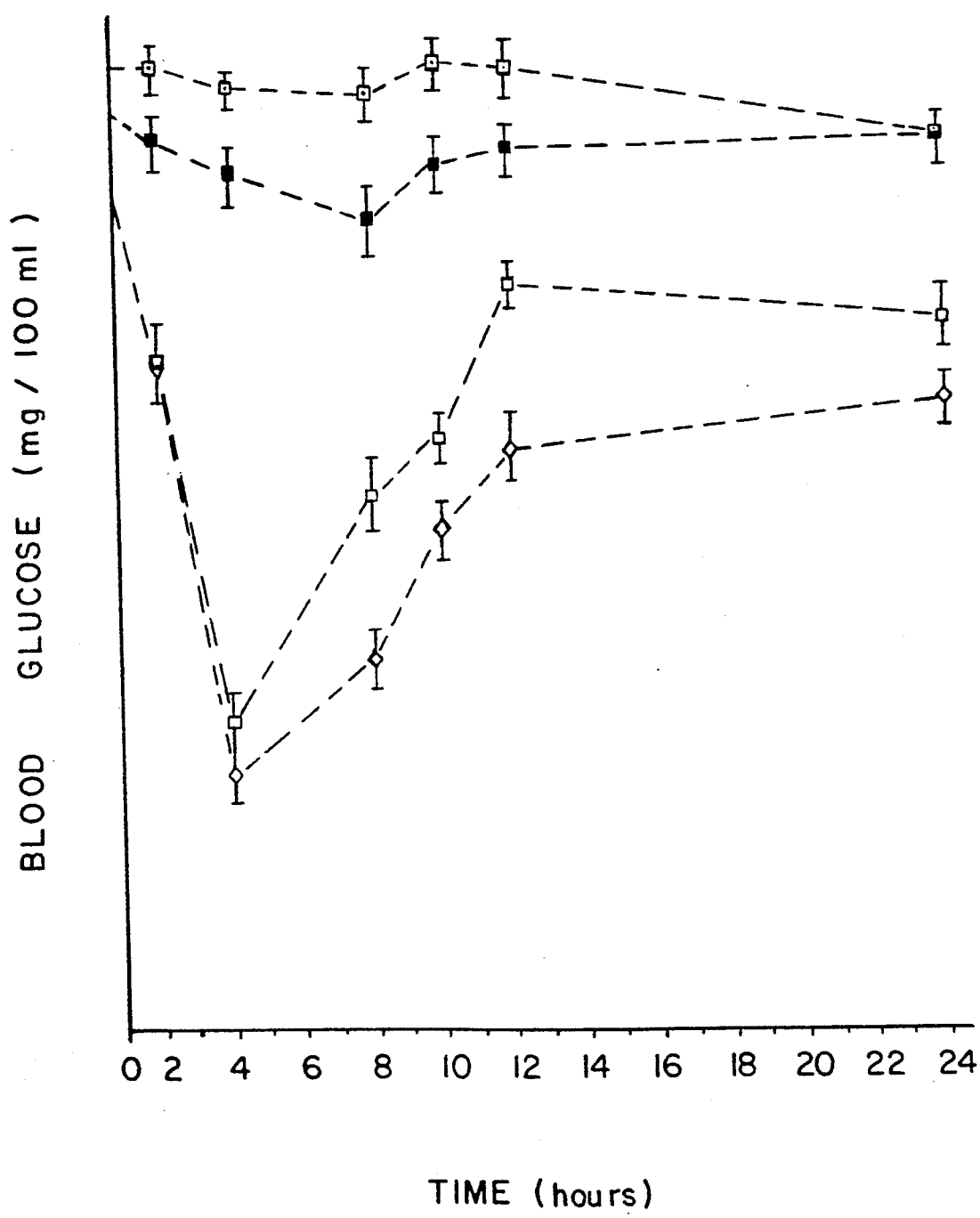

FIG. 4 graphically illustrates the activity of dioscoretine (20 mg/kg) and extracts of *D. dumetorum* (100 mg/kg) and tolbutamide (500 mg/kg) on the blood glucose level of rabbits having alloxan-induced diabetes. (---▣---) saline control; (---◇---) dioscoretin; (---□---) aqueous fraction of the methannol extracts (---■---) tolbutamide.

5. DETAILED DESCRIPTION OF THE INVENTION

5.1. PROCESS FOR PREPARING DIOSCORETINE

According to a preferred embodiment of the present invention, dioscdretine is prepared as follows: tubers of *D. dumetorum* are extracted with methanol, for example, using a Soxhlet extractor, usually with heating, although room temperature is also suitable. Preferably, the tubers may be first cut into pieces, dried and ground to a powdered form. The extract is concentrated to a viscous, sticky liquid under reduced pressure. The residue is taken up into 3% (v/v) HCl and filtered. The acidic solution is neutralized and the pH raised to about pH 9, for example, with dilute ammonium hydroxide. The basic solution is extracted 5 times with chloroform ($CHCl_3$) and 2 times with methylene dichloride ($CH_2Cl_2$). The aqueous fraction contains the dioscoretine of the invention.

According to an alternative embodiment, dioscoretine can be prepared by extraction of *D. dumetorum* tubers using a weak, acidic solution as follows: The tubers, preferably cut up and/or macerated, are placed in a weak acid solution such as 10% acetic formic, tartaric or hydrochloric acid, in methanol and the mixture allowed to stand for about 4 hours. The extract is concentrated by evaporation to about one-quarter of the original volume. Concentrated $NH_4OH$ is added to precipitate the dioscoretine containing fraction and the precipitate is collected, for example, by centrifugation.

The bioactive dioscoretine is isolated from the aqueous fraction (or from the precipitate) using a silica gel chromatographic column eluted with chloroform:methanol, preferably about 4:1, although about 9:1 is also useful.

Additionally, dioscoretine of the present invention can be obtained by semi-synthetic methods from other alkaloids such as dihydrodioscorine or dioscorine (See Corley et al., supra). In practice, dioscoretine can be obtained by acid hydrolysis of dihydrodioscorine or by reduction of dioscorine, e.g.using sodium borohydride, etc., followed by acid hydrolysis.

5.2. CHARACTERIZATION OF DIOSCORETINE

The dioscoretine compound of the present invention gives a positive Dragendorff reaction, indicative of an alkaloidal structure (Harborne, 1984, Phytochemical Methods, 2d Ed., Chaman and Hall, New York, pp. 196-97).

Based on its MS, IR, $^3H$ NMR and carbon-13 NMR, the structure shown in FIG. 1 has been assigned to dioscoretine. Dioscoretine belongs to the general class of alkaloids, more particularly, isoquinuclidine alkaloids. Dioscoretine is soluble in methanol and water and sparingly soluble in ethanol.

In addition dioscoretine possesses functional moieties which can be exploited for the development of additional new compounds which may possess lower toxicity. In particular, the hydroxyl and/or carboxyl groups can be modified by alkylation, dealkylation, acetylation or glycosylating, etc. to improve the pharmacodynamics and pharmcokinetics of the dioscoretine compound. Similarly, the methyl group attached to the nitrogen can be replaced by an alkyl group such as ethyl, propyl and butyl groups.

As demonstrated in Example 7, infra, dioscoretine is a potent biological agent having an $LD_{50}$ of about 580 mg/kg in mice.

5.3. USES OF DIOSCORETINE

Due to the potent activity of dioscoretine as a hypoglycemic agent (see Section 7.1, infra), it is advantageously useful in veterinary and human medicine for therapeutic treatment of diabetes mellitus. Additionally, dioscoretine can advantageously be used as a hypoglygemic agent to reduce the blood glucose level in situations of acute stress such as experienced by patients with hyperthermia, trauma, sepsis, and burns and undergoing general anesthesia. Hyperglycemia sometimes associated with severe head injury, cerebral thrombosis, encephalitis and heat stroke can also be therapeutically treated with dioscoretine of the invention. Additionally, dioscoretine may be useful as a hypoglycemic agent for rare congenital metabolic glycogen storage disease associated with hyperglycemia.

Although the present inventor does not wish to be limited to any particular mechanism of action to explain the hypoglycemic activity of dioscoretine, because such activity appears to be indirect, it is envisaged that dioscoretine may advantageously be useful for treatment of both insulin—dependent or type I diabetes (formerly termed juvenile—onset or ketosis-prone diabetes) and non-insulated-dependent or type II diabetes (formerly termed adult-onset, maturity-onset or nonketotic diabetes).

Dioscoretine can be administered in an effective amount either in the form shown in FIG. 1 or as a pharmaceutically acceptable salt such as a hydrochloride, hydrobromide, phosphate, sulfate, acetate, benzoate, malate, etc.

When administered to a mammal for veterinary use or to a human for clinical use, the dioscoretine or pharmaceutically acceptable salt thereof may be used alone, or may be combined with any physiologically acceptable carrier such as water, an aqueous solution, normal saline, or other physiologically acceptable excipient. In general, the dosage would range from about 20 to about 100 mg/kg body weight of the human or animal to be treated.

The dioscoretine or pharmaceutically acceptable salt thereof can be administered by a number of routes, including, but not limited to: orally, injection including, but not limited to intravenously, intraperitoneally, subcutaneously, intramuscularly, etc. Additionally, dioscoretine or a pharmaceutically acceptable salt thereof can be administered via a subdermal implant to provide a slow release medicament for therapeutic treatment of diabetes mellitus.

Additionally, dioscoretine or a pharmaceutically acceptable salt thereof, can be administered in conjunction with another hypoglycemic including such as insulin, or a sulfonylurea such as acetohexamide, chloropropamide, tolazamide, tolbutamide, etc.

Finally, dioscoretine and compositions containing dioscoretine or pharmaceutically acceptable salts thereof can be used for research purposes, for example, to investigate the mechanism and activity of hypoglycemic agents.

The following series of Examples are presented by way of illustration and not by way of limitation on the scope of the invention.

6. EXTRACTION AND ISOLATION OF DISCORETINE

Tubers of Dioscorea dumetorum were collected at Ankpa Local Government Area in the Benue State of Nigeria. The authenticity of the material was confirmed by Dr. J. C. Okafor of the Forestry Division Anambra State ministry of Agriculture, Enugu. A voucher specimen has been deposited at the Pharmacy Herbarium University of Nigeria, Nsukka. Tubers of *D. dumetorum* were sliced into chips and sun dried for 4 days.

1.5 kg of the powdered tuber of *D. dumetorum* was extracted in 16 batches with 10/1 of methanol (MeOH) in a Soxlet apparatus. The bulk extract was concentrated to a viscous liquid (about, 500 ml) under reduced pressure. The sticky residue was taken up in 1 l of 3% v/v HCl and filtered. The acidic aqueous solution was extracted with $CHCl_3$, then basified to pH 9 with dilute $NH_4OH$ and reextracted with 5/1 $CHCl_3$ and $3 \times 500$ ml $CH_2Cl_2$. The combined organic fractions and the aqueous fraction were separately concentrated to dryness.

10 g of the residue from the aqueous fraction was packed onto a silica gel column and eluted with mixtures of $CHCl_3$ and various concentrations of MeOH. A homogeneous product (425 mg), identified as dioscoretine (1), was obtained when the column was eluted with $CHCl_3$-MeOH (4:1).

7. BIOLOGICAL ACTIVITY OF DIOSCORETINE HYPOGLYCEMIC ACTIVITY IN NORMAL AND DIABETIC ANIMALS

The following experiments demonstrate that dioscoretine produces a significant and consistent hypoglycemic effect on both normal and diabetic animals.

In one series of experiments, the hypoglycemic activity of dioscoretine was assessed and compared with that of the aqueous and organic ($CHCl_3$) fractions of the methanol extract of *D. dumetorum* tubers using normal female rats (Wistar), weighing an average of $200 \pm 22$ g. The animals were fasted for twenty hours but had access to water *ad libitium.*

Dioscoretine, isolated as described in Section 6, supra, the chloroform ($CHCl_3$) fraction and the aqueous fraction of the methanol extract of *D. dumetorum* tubers (see Section 6, supra) in normal saline were administered intraperitoneally (i.p.) to three groups (6 animals each) of experimental animals as follows: Group 1, chloroform, 100 mg/kg; Group 2, aqueous fraction, 100 mg/kg; and Group 3, dioscoretine, 20 mg/kg. A fourth group of animals which received saline only served as controls. Blood samples were collected for glucose determination from the jugular vein at intervals of 30 minutes during the first 2 hours and then at 4 hours, 8 hours and 12 hours folloWing the administration. Animals were anaesthetized with pentobarbitone (i.p. 50 mg/kg) before blood sampling. The glucose concentration was determined by the O-toludine method as described by Bauner et al. (1974, Clinical Laboratory Methods, pp. 381–385, C.V. Mosby Company, St. Louis, MO). The percentage decrease in glycemia was calculated using the formula:

$$\% \text{ decreased glycemia} = \frac{Go - Gx}{Go} \times 200$$

where Go and Gx are the values of initial glycemia (Go) and the glycemia at different time intervals respectively.

Results are presented in Table 1 and illustrated in FIG. 2.

TABLE 1

HYPOGLYCEMIC ACTIVITY OF DIOSCORETINE AND FRACTIONS OF THE ALCOHOLIC EXTRACT OF *D. DUMETORUM*

| Treatment | Blood Glucose Level mg % (percent difference) at various times ||||||| 
|---|---|---|---|---|---|---|---|
| | 30 mins. | 60 mins. | 90 mins. | 2 hours | 4 hours | 8 hours | 12 hours |
| Basal glucose (Normal saline) | 96.5 ± 4.0 | 91.9 ± 3.2 | 91.4 ± 2.5 | 90.4 ± 3.0 | 89.6 ± 2.8 | 94.6 ± 2.5 | 96.0 ± 3.0 |
| Chloroform fraction | 118.0 ± 2.0 | 130.1 ± 1.8 | 141.4 ± 0.05 | 159.8 ± 1.8 | 183.2 ± 2.3 | 172.3 ± 1.7 | 163.1 ± 2.4 |
| Aqueous fraction | 86.1 ± 2.0 | 75.3 ± 0.9 | 70.8 ± 1.2 | 66.4 ± 1.8 | 62.3 ± 2.1 | 74.6 ± 0.8 | 85.0 ± 22.0 |
| Dioscoretine | 80.4 ± 3.0 | 71.6 ± 2.3 | 66.1 ± 2.0 | 60.2 ± 1.9 | 51.6 ± 1.6 | 68.4 ± 3.1 | 62.4 ± 1.8 |

The results show that the aqueous fraction of the alcoholic extract of Dioscorea at a dose of 100 mg/kg lowered the blood sugar from a basal value of 95 mg % to 86.1 mg % in 30 minutes and a maximum reduction to 60.4 mg % after 4 hours (FIG. 2). Dioscoretine followed the hypoglycemic pattern of the aqueous fraction. At a lower dose (20 mg/kg) the compound demonstrated stronger hypoglycemic activity (FIG. 1) with a blood sugar level at 51.6 mg % at the 4th hour. The maximum reduction was obtained in both the aqueous extract and dioscoretine at the 4th hour. At 12 hours post-administration of dioscoretine blood glucose remained at 62.4 mg % still below the initial value of about $96.0 \pm 3.0$ mg%.

In contrast, the chloroform fraction at the same dose raised the initial glucose level within 30 minutes from 118 mg and to 183 mg % at the 4th hour.

In another series of experiments, the biological activity of dioscoretine, prepared as described in Section 6, supra, was assessed in normal and diabetic rabbits and compared with that of the aqueous fraction and the $CHCl_3$ fraction of the methanol extract of *D. dumetorum* tubers. For administration to experimental animals, the dioscoretine was suspended in 1% Tween ® 20. Two g of the dried aqueous fraction was suspended with 1% Tween ® 20 in 100 ml of normal saline and appropriate dose dilutions made with normal saline to provide for a total volume of 5 ml. Two g of the $CHCl_3$ fraction of the method extract (total yield of 6.2 g) were similarly treated. The vehicle control was prepared by adding 1% Tween ® 20 to normal saline.

Local strains of adult healthy rabbits weighing between 1.2–1.8 kg were used for this series of experiments. In all experiments reported below, animals were maintained for 7 days with free access to food and water before the beginning of the experiments.

Diabetes was experimentally induced in one group of animals by the administration of alloxan. The animals were injected intravenously with 150 mg/kg body weight of alloxan monohydrate. The alloxan was freshly prepared as 10% solution in distilled $H_2O$. Eight days after injection of the alloxan, blood glucose levels of all the surviving rabbits were determined. Only rabbits with glucose levels above 350 mg/100 ml on 12 hours fast were considered diabetic (7) and employed for the assay.

A number of normal animals was divided into 4 treatment groups of 6 animals each. Group 1, received an i.p. injection (5 ml) of dioscoretine at 20 mg/kg; Group 2, aqueous fraction of the methanol extract of *D. Dumetorum* at 100 mg/kg; Group 3, chloroform extract of the methanol extract of *D. Dumetorum* at 100 mg/kg; and Group 4, tolbutamide at 500 mg/kg. A fifth group of animals which received only the vehicle served as controls.

The 18 diabetic animals were divided into 3 treatment groups of 6 animals each. Group 1, received an i.p. injection (5 ml) of dioscoretine at 20 mg/kg; Group 2, aqueous fraction of the methanol extract of *D. Dumetorum* at 100 mg/kg; and Group 3, tolbutamide at 500 m/kg. Another group of 6 animals which received only the vehicle served as the controls.

The results are illustrated in FIGS. 3 and 4 for normal and diabetic animals respectively.

As shown in FIG. 3, dioscoretine, at 20 mg/kg, significantly reduced the fasting blood sugar of normal animals from 112 mg/100 ml (i.e. to less 50% of normal blood glucose) at 4 hours post-administration ($P<05$). At 10 hours the blood glucose returned to about 90 mg/100 ml and did not change significantly at 24 hours. Similarly the aqueous fraction of the methanol extract of the tubers significantly ($P<0.001$) lowered the fasting of blood glucose from 126 mg/100 ml at zero hour to 78 mg/10 ml after 4 hours. At 12 hours the blood glucose was 103 mg/100 ml and did not change significantly after 24 hours (105 mg/100 ml).

Tolbutamide, a known hypoglycemic agent, at 2500 mg/kg, caused a significant ($P<0.05$) reduction of the fasting blood sugar from 115 mg/100 ml at zero time to the lowest value of about 56 mgl/100 ml at 4 hours post-administration. The blood glucose returned to near the normal values in 12 hours and remained significantly unchanged after 24 hours. Two control animals that received Tween ® 20 in normal saline showed no significant difference in the blood glucose at various time intervals.

As shown in FIG. 4, when administered to diabetic animals, dioscoretine consistently significantly ($P<0.001$) reduced the fasting blood sugar at the various time intervals when compared with the zero hour glucose level. The lowest value of 286 mg/100 ml was observed at the 4th hour. At 8, 10, 12 and 24 hours the blood glucose increased significantly relative to the 4 hour level but these values were still significantly lower than the blood glucose level at the zero hour. The diabetic group treated with the aqueous fraction showed significant ($P<0.05$) decrease in the blood glucose at 2, 4, 8, 10 and 12 hours when compared to the zero hour level. The lowest blood glucose was observed at 4 hours (305 mg/100 ml). At 24 hours the glucose level of 440 mg/100 ml was still significantly lower ($P<0.001$) than the blood glucose at the zero hour.

Tolbutamide, at 500 mg/kg, caused no significant decrease in the blood sugar levels of the diabetic animals at the various times when compared to the zero hour level of 515 mg/100 ml. At 24 hours animals treated with tolbutamide gave the same mean blood glucose level as the vehicle control group that received normal saline and Tween ® (FIG. 4). Control diabetic animals that received only 1% Tween ® 20 in normal saline no significant difference in the blood sugar at 0, 2, 4, 8, 10 up to 24 hours.

Based on the results presented in FIGS. 3 and 4, it appears that dioscoretine can be classified as a direct hypoglycemic agent, although it may also exert its hypoglycemic effects via an indirect mechanism. As shown in FIG. 4, dioscoretine significantly reduced the blood glucose level when administered to alloxan-treated animals, i.e. animals in which pancreatic $\beta$-cells were permanently destroyed. In contrast, tolbutamide, a hypoglycemic agent acting via an indirect mechanism by stimulating $\beta$-cells, had no significant hypoglycemic activity when administered to alloxan-treated animals.

7.2 ACUTE TOXICITY

The acute toxicity of dioscoretine, the aqueous fraction and the $CHCl_3$ fraction of the methanol extract of *D. dumetoreum* tubers was assessed as follows:

36 adult albino mice of either sex weighing 20–25 g were deprived of food for 12 hours (overnight) but allowed access to $H_2O$. They were divided into groups of six animals, with an equal number of both sexes in a group. Animals in each group were given a predetermined dose of the test substance by i.p. injection. The number of mice that died within 12 hours was noted for each group, and the $LD_{50}$ was calculated by the graphical method of Miller and Tainter (1944, Proc. Soc. Exp. Biol. Med. 57:261–266). The animals were also observed for general effects and behavioral changes.

The $CHCl_3$ fraction was most toxic with $LD_{50}$ 238 mg/kg. Dioscoretine is a potent substance having an $LD_{50}$ of about 580 mg/kg. The aqueous fraction is the least toxic with $LD_{50}$ of 1400 mg/kg of the substances tested. The mice that received the $CHCl_3$ fraction became restless soon after receiving the lethal dose, darted around the cages, squeaked, licked their paws and suffered from generalized convulsions.

Animals which received the LD50 dose of dioscoretine or the aqueous extract were sluggish in movement and clumping together at the corners of the cage, exhibiting piloerection and prostration. At the highest experimental dose (2.20 g/kg), the aqueous extract caused convulsions in the majority of the animals (4/6) and death followed within 30 minutes.

When the various doses found to be toxic to the mice (the $LD_{50}$ doses) were administered to rabbits, no notable effects were observed. It was, however, not possible to determine the $LD_{50}$ of the test substances in rabbits due to lack of material.

The present invention is not be limited in scope by the the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the scope of the appended claims.

What is claimed is:

1. A compound, dioscoretine, having the structural formula:

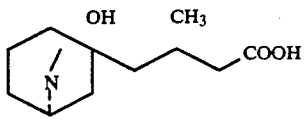

or a pharmaceutically acceptable salt thereof.

2. The compound of claim 1, in which the pharmaceutically acceptable salt is selected from the group consisting of hydrochloride, hydrobromide, phosphate, sulfate, acetate, benzoate and malate.

3. A pharmaceutical composition for use as a hypoglycemic agent in mammals, comprising a therapeutically effective amount of the compound of claim 1 together with a physiologically suitable carrier.

4. A method for reducing the blood glucose level of a host, comprising administering to the host an effective amount of the composition of claim 1.

5. A method for reducing the blood glucose level of a host, comprising administering to the host an effective amount of the composition of claim 3.

6. A method for treatment of diabetes mellitus, comprising administering to a host suffering from diabetes mellitus a therapeutically effective amount of the composition of claim 1.

7. A method for treatment of diabetes mellitus, comprising administering to a host suffering from diabetes mellitus a therapeutically effective amount of the composition of claim 3.

8. The method according to claim 6, in which the host is a non-human animal.

9. The method according to claim 6, in which the host is a human.

10. The method according to claim 7, in which the host is a non-human animal.

11. The method according to claim 7, in which the host is a human.

12. A method for treatment of diabetes mellitus, comprising administering to a host suffering from diabetes mellitus:
(a) a therapeutically effective amount of dioscoretine having the structural formula:

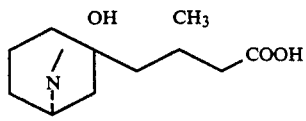

or a pharmaceutically acceptable salt thereof; and
(b) a therapeutically effective amount of a sulfonylurea selected from the group consisting of acetohexamide, chloropropamide, tolazamide and tolbutamide.

13. A method for treatment of diabetes mellitus, comprising administering to a host suffering from diabetes mellitus:
(a) a therapeutically effective amount of dioscoretine having the structural formula:

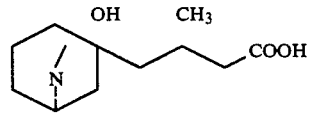

or a pharmaceutically acceptable salt thereof; and
(b) a therapeutically effective amount of insulin.

* * * * *